US009681614B2

(12) United States Patent
Hofstede et al.

(10) Patent No.: US 9,681,614 B2
(45) Date of Patent: Jun. 20, 2017

(54) CLOSTEROVIRUS-RESISTANT MELON PLANTS

(75) Inventors: René Johannes Maria Hofstede, Boven-Leeuwen (NL); Petrus Jacobus Kraakman, Aguadulce (ES); Jeroen Sebastiaan De Vries, The Hague (NL)

(73) Assignee: Monsanto Invest B.V., Bergschenhoek (NL)

( * ) Notice: Subject to any disclaimer, the term of this patent is extended or adjusted under 35 U.S.C. 154(b) by 1180 days.

(21) Appl. No.: 12/140,405

(22) Filed: Jun. 17, 2008

(65) Prior Publication Data

US 2009/0013435 A1 Jan. 8, 2009

Related U.S. Application Data

(63) Continuation of application No. PCT/NL2006/000650, filed on Dec. 21, 2006.

(30) Foreign Application Priority Data

Dec. 21, 2005 (EP) .................................... 05077953

(51) Int. Cl.
*A01H 5/08* (2006.01)
*A01H 1/00* (2006.01)
(52) U.S. Cl.
CPC ................ *A01H 1/00* (2013.01); *A01H 5/08* (2013.01)
(58) Field of Classification Search
None
See application file for complete search history.

(56) References Cited

FOREIGN PATENT DOCUMENTS

| EP | 0 974 672 A1 | 1/2000 |
| EP | 1 188 833 A1 | 3/2002 |
| WO | WO 00/24906 | 5/2000 |

OTHER PUBLICATIONS

McCreight 2000 HortScience 35:1118-1120, provided by Applicant.*
Jon Slate 2005 Molecular Ecology 14:363-379.*
McCreight, J.D., et al., "Potential New Sources of Genetic Resistance in Melon to Cucurbit Yellow Stunting Disorder Virus," Proceedings of the IXth EUCARPIA meeting on genetics and breeding of Cucurbitaceae (Pitrat M, ed), INRA, Avignon (France), May 21-24, 2008, pp. 173-180.
McCreight, J.D., "Progress in Breeding Melon for Resistance to Lettuce Infectious Yellows Virus," Proceedings of Cucurbitaceae 2004, 8th Eucarpia meeting on Cucurbit Genetics and Breeding; Palacky University in Olomouc, Czech Republic, Jul. 17, 2004; pp. 219-224.
Bai et al., "QTLs for Tomato Powdery Mildew Resistance (*Oidium lycopersici*) in Lycopersicon parviflorum G1.1601 Co-localize with Two Qualitative Powdery Mildew Resistance Genes," *Mol. Plant Microbe Interactions*, 16(2):169-176 (2003).
Célix et al., "Characterization of Cucurbit Yellow Stunting Disorder Virus, . . . ," *Phytopathology*, St. Paul, MN, 86(12):1370-1376 (1996).
Danin-Poleg et al., "Search for molecular markers associated with resistance to viruses in melon," *Acta Hort.*, 510:399-403 (2000).
Diaz et al., "Potential sources of resistance for melon to nonpersistently aphid-borne viruses," *Plant Disease*, 87(8):960-964 (2003).
Havey et al., "Differential transmission of the Cucumis organellar genomes," *Theor. Appl. Gen.*, 97:122-128 (1998).
López-Sesé and Gómez-Guillamón, "Resistance to Cucurbit Yellow Stunting Disorder Virus (CYSDV) in *Cucumis melo* L," *Hortscience*, 35(1):110-113 (2000).
McCreight, "Screening for Lettuce Infectious Yellows Virus Resistance in Melon," *Fifth Eucarpia Cucurbitaceae Symposium*, Jul. 27-31, 1992, Research Institute of Vegetable Crops Skierniewice and Warsaw University of Agriculture, Warsaw, Poland, pp. 160-162.
McCreight, "Resistance to Lettuce Infectious Yellows Virus in Melon," *HortScience*, 33(3):533 (1998) (Abstract).
McCreight, "Breeding Melon for Resistance to Lettuce Infectious Yellows Virus," *Cucurbitaceae '98*, pp. 241-247 (1998).
McCreight, "Inheritance of Resistance to Lettuce Infectious Yellows Virus in Melon," *HortScience*, 35:1118-1120 (2000).
McCreight, "Progress in breeding melon for resistance to lettuce infectious yellows virus," *Progress in Cucurbit Genetics and Breeding Research, Proceedings of Cucurbitaceae 2004*, the 8th Eucarpia Meeting on Cucurbit Genetics and Breeding, Olomouc, Czech Republic, Jul. 12-17, 2004, Palacky University, Olomouc, pp. 219-222.
Nuez et al., "Genetics of Melon yellows virus resistance derived from *Cucumis melo* ssp. *agrestis*," *Eur. J. Plant Path.*, 105:453-464 (1999).
Sinclair, "Screening for resistance to cucurbit yellow stunting disorder virus, . . . ," Ph.D. thesis submitted to Texas A&M University (2003).
Soria et al., "Resistance mechanisms of *Cucumis melo* var. *agrestis* against *Trialeurodes vaporariorum* and their use to control a closterovirus that causes a yellowing disease of melon," *Plant Path.*, 45:761-766 (1996).
Van Berloo et al., "Resistance QTL confirmed through development of QTL-NILs for barley leaf rust resistance," *Mol. Breeding*, 8:187-195 (2001).
Boissot, et al., "Insect resistance in Cucumis melo accession 90625," in Acta Hort 510, ISHS 2000, 297-304.

(Continued)

Primary Examiner — Brent Page
(74) Attorney, Agent, or Firm — Dentons US LLP (57) ABSTRACT

The present invention relates to plant of the species *Cucumis melo*, said plant comprising a genetic element derived from a plant of the species *Cucumis melo* var. *agrestis*, which genetic element comprises a closterovirus-resistance-conferring QTL or a closterovirus-resistance-conferring part thereof linked to at least one marker located on the chromosome equivalent to linkage group (LG) 6 of melon accession PI 313970, wherein said plant is not melon accession PI 313970.

20 Claims, 1 Drawing Sheet

(56) References Cited

OTHER PUBLICATIONS

Dogimont, et al., "Sources of Resistance to Cucurbit Aphid-borne Yellows Luteovirus in a Melon Germ Plasm Collection," Plant Disease, Dec. 1996, 1379-1382.
De Vries et al., "Screening Melon Lines with AFLP Markers Linked to CYSDV QTL1," Report Monsanto, Aug. 2010.
Expert Declaration of Jeroen De Vries; Opposition EP 1 962 578 B1; Oct. 30, 2012.
Ford-Lloyd et al., pp. 55-61; in "Plant genetic resources: an introduction to their conservation and use," Edward Arnold publishers, London, 1986.
KeyGene primer codes; EPO-DG2; Aug. 10, 2010.
McCreight; Molecular and Phenotypic Variation in Melon PI 313970; Proc. Cucurbitaceae, ISHS 2000, *Acta Hort* 510:235-239; 2000.
McGlasson et al., Fruit-Set Patterns and Fruit Growth in Cantaloupe (*Cucumis melo* L. var. *reticulatis* Naud.); *American Society for Horticultural Science* v.83; pp. 495-505; 1963.
Pelemen; "Application of the AFLP® Technique in Marker Assisted Breeding". Chapter 14; in Final compendium of the Research Project Development, optimisation and validation of molecular tools for assessment of biodiversity in forest trees; 4 pages.
PI 313970 Database *Cucumis melo* subsp. *Melo—VIR 5682—*India; 2 pgs.; downloaded from www.ars-grin.gov/cgi-bin/npgs/acc/display.pl?1234456 on Jan. 20, 2012.
Reitsma, "Cucumis" section from poster presentation of North Central Regional Plant Introduction Station, Ames, IA, downloaded Feb. 2, 2012 from http://www.ars.usda.gov/SP2UserFiles/Place/50301000/Posters/Vegetables.pdf ; Feb. 2, 2012.
Vos et al., :AFLP: a new technique for DNA fingerprinting, *Nucleic Acids Research*; vol. 23, No. 21; pp. 4407-4414; 1995.

\* cited by examiner

CLOSTEROVIRUS-RESISTANT MELON PLANTS

RELATED APPLICATIONS

This application is a continuation of PCT application no. PCT/NL2006/000650, designating the United States and filed Dec. 21, 2006; which claims the benefit of the filing date of European application no. EP 05077953.7, filed Dec. 21, 2005; each of which is hereby incorporated herein by reference in its entirety for all purposes.

FIELD

The present invention relates to plant breeding and molecular biology. More specifically, the present invention relates to a quantitative trait locus (QTL) associated with resistance to closterovirus in melon, to a closterovirus-resistant melon plant comprising said QTL and to a method of producing a closterovirus-resistant melon plant.

BACKGROUND

Cucurbit yellow stunting disorder virus (CYSDV) is a closterovirus transmitted in nature by the whitefly *Bemisia tabaci*. CYSDV was first detected in 1982 in the United Arab Emirates, and since then, it has been found in Spain, Portugal Morocco, Lebanon and North America extensively affecting cucurbit crops. CYSDV induces interveinal chlorotic spots in mature leaves which may enlarge and eventually fuse together producing yellowing of the entire leaf except for the veins that remain green. Yellowing symptoms are accompanied by substantial reduction in fruit yield and quality and, therefore, the virus has a high economic importance.

The control of CYSDV is currently based on chemical treatments against its vector and preventive cultural practices, both with limited success. The use of genetically resistant cultivars is a good option for CYSDV control.

Resistant accessions of melon (*Cucumis melo*), such as accession C-105 (TGR-1551), have recently been found (López-Sesé et al., 2000). In principal, genetic material from such accessions that comprises the genetic information responsible for the CYSDV resistance could be introgressed into commercial cultivars. However these attempts have hitherto been unsuccessful for unknown reasons. Therefore no resistant melon cultivar is at present commercially available. It is believed that the practical problem of developing resistant cultivars is hampered by two factors. Firstly, it is not known whether such specific accession as C-105 provides the best source of resistance. If the result is a cultivar exhibiting partial resistance, the result of the market introduction of such a cultivar may lead to the development of resistance-breaking viral strains. Furthermore, the possibility of stably fixing the resistance trait in the genome of the target plant remains to be determined. Thus, choosing a particular source of resistance does not guarantee success and may even hold various risks. In addition, the introgression itself involves a substantial breeding effort, and includes the development and performance of bioassays to follow resistant offspring plants. In effect, the development of a resistant cultivar is commercially costly undertaking and any program may be early abandoned when results fail to precipitate.

In order to reduce the uncertainties and work involved in developing a resistant cultivar, it would be beneficial to have a simple genomic marker for the resistance trait. Such a marker could then be used in marker assisted selection (MAS) procedures as part of a dedicated breeding program. Whether such a marker can be found is partly determined by genomic structure of the resistance trait. If the trait is multi-genic, it is not likely that a single marker is found that may reliably be used in MAS procedures. Moreover, the development of the marker(s) themselves then mounts to a significant undertaking, possibly overshadowing the costs and time involved in a straightforward breeding program.

However, once a suitable resistance source is identified and a marker is developed, the new resistant plants can be easily traced, which increases their commercial value.

SUMMARY

The present invention now relates in a first aspect to a plant of the species *Cucumis melo*, said plant comprising a genetic element derived from a plant of the species *Cucumis melo* var. *agrestis*, which genetic element comprises a closterovirus-resistance-conferring QTL or a closterovirus-resistance-conferring part thereof linked to at least one marker located on the chromosome equivalent to linkage group (LG) 6 of melon accession PI 313970, wherein said plant is not melon accession PI 313970. Wild accessions of *Cucumis melo* plants that are resistant to closterovirus are known to occur in nature (e.g. melon accession C-105, see above). Melon plants of the species *Cucumis melo* var. *agrestis*, e.g. such as accession PI313970), however, were not previously associated with closterovirus resistance. The present inventors have now found that the resistance in this variety is linked to a defined genetic region or QTL (hereinafter also indicated as QTL-1). A melon plant of the invention comprises a genetic element derived from a plant of the species *Cucumis melo* var. *agrestis*, more preferably a closterovirus-resistant plant of said species, still more preferably from melon accession PI313970, which genetic element comprises the closterovirus-resistance-conferring QTL as identified by the present inventors.

A plant of the present invention is preferably a cultivar, but is not necessarily restricted to a specific strain. A plant of the present invention is preferably a plant having commercially valuable characteristics, including, but not limited to melon plants having commercially valuable fruit or seed characteristics.

The plant of the invention may comprise the referred QTL in a form wherein the resistance genes are present on a single allele, or in a form wherein the resistance genes are present on both alleles. Thus, the plants of the present invention may be heterozygous or homozygous for the resistance traits, preferably homozygous. It should be noted in this respect that although heterozygous plants do not express a recessive trait, new plants that comprise the QTL, or closterovirus-resistance conferring genes comprised therein, in heterozygous form constitute an important intermediate product in a program to develop a resistant cultivar.

Figure 1:
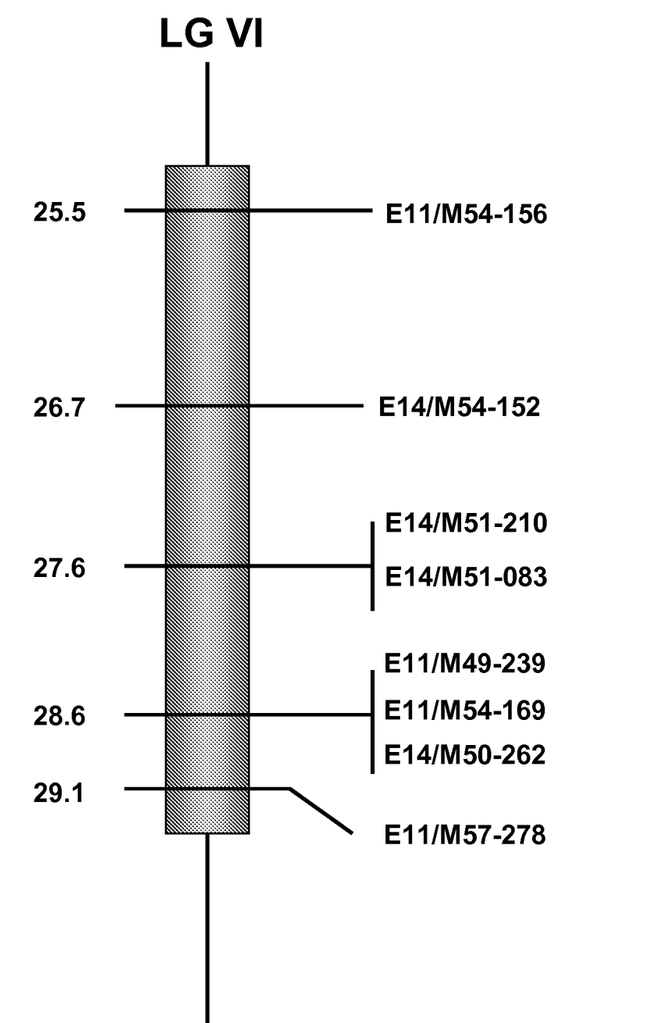
FIG. 1 represents a linkage map indicating the relative position of the various markers as described herein. Relative positions on linkage group 6 (LG-VI) are provided in cM. Only markers with known positions are indicated.

The closterovirus-resistance-conferring QTL of the present invention (QTL-1) is preferably associated with a marker that is located on the chromosome equivalent of linkage group (LG) 6 and stretches from position 25.5 cM to 29.1 cM, preferably at about position 28.6 cM on the Map as presented in FIG. 1. The region where the QTL is located is strongly linked to markers E11/M54-156, E14/M54-152, E14/M51-210, E14/M51-083, E11/M49-239, E11/M54-169, E14/M50-262, E11/M57-278, E11/M54-163 and/or E11/M49-072, more preferably to marker E11/M49-239.

A closterovirus-resistant plant of the species *Cucumis melo* may be any *Cucumis melo* species, with the proviso that the plant is not melon accession PI313970. Thus, in a plant of the invention, the closterovirus-resistance-conferring QTL as defined herein is not in its natural genetic background of melon accession PI313970. An another preferred embodiment, a plant of the present invention is not a plant of the species Cucumis melo var. agrestis. An another preferred embodiment, a plant of the present invention is melon cultivar.

In another aspect, the present invention relates to a part of a plant of the invention, such as a seed.

In another aspect, the present invention relates to a quantitative trait locus (QTL) associated with resistance to closterovirus in a plant of melon accession PI313970. The closterovirus-resistance-conferring QTL-1 is associated with markers E11/M54-156 (cis), E14/M54-152 (cis), E14/M51-210 (cis), E14/M51-083 (trans), E11/M49-239 (cis), E11/M54-169 (cis), E14/M50-262 (trans), E11/M57-278 (cis), E11/M54-163 (cis) and/or E11/M49-072 (trans), more preferably to marker E11/M49-239, is located on the chromosome equivalent of linkage group (LG) 6, and stretches from position 25.5 cM to 29.1 cM. As a physical entity, QTL-1 is part of a nucleic acid, either isolated or in a genomic background, and is capable of conferring closterovirus-resistance to a plant in the genome of which it is introduced, preferably, in a location of the genome that is homologous to the location in the genome of melon accession PI313970 where it was first detected and as specified herein.

The markers themselves may be used in aspects of the invention relating to marker-assisted-selection and methods wherein plants having the QTL are traced. The markers used in such aspects may either be trans, or cis markers. A trans marker indicates a polymorphism resulting from introgression of exogenous (donor) DNA into a recipient plant's genome, which polymorphism is linked in cis with the recipient genome, i.e. linked with the opposite allele. Thus, cis markers are linked with the allele of interest (i.e. from the donor), while trans markers are linked with the opposite allele (i.e. from the recipient). However, both are predictive for the resistant allele encoded by the QTL of interest.

In another aspect the invention relates to a method for producing a plant of the present invention comprising introducing into a closterovirus-susceptible melon plant a genetic element derived from a plant of the species Cucumis melo var. agrestis, more preferably from melon accession PI313970, which genetic element comprises the closterovirus-resistance-conferring QTL as described in more detail above.

The introduction of the QTL, or an isolated nucleic acid comprising the QTL of the invention, or a resistance-conferring part thereof, into a melon plant may be performed by any method known to the artisan. Preferably the introduction is performed by introgression (crossing). In such an embodiment, a method of the present invention comprises the step of crossing a plant of melon accession PI313970, or a closterovirus-resistant derivative thereof, with a closterovirus-susceptible melon plant; harvesting seed from the cross, growing said seed to produce F1 progeny plants; selfing or backcrossing said F1 progeny plants with the donor or recipient parent to produce F2 seeds; growing said F2 seeds to produce F2 progeny plants; determining the presence in the genome of at least one of said F2 progeny plants of a closterovirus-resistance-conferring QTL, wherein said QTL is characterized as described in more detail above, wherein the presence of said QTL is confirmed by detecting the presence in the DNA of said at least one F2 progeny plants of a marker linked to said QTL.

DETAILED DESCRIPTION OF CERTAIN PREFERRED EMBODIMENTS

The term "melon" as used herein refers to the species Cucumis melo L. (syn. Cucumis chito; Cucumis dudaim aegyptiacus; Cucumis flexuosus; Cucumis melo var. acidulus; Cucumis melo var. aegyptiacus; Cucumis melo var. ameri; Cucumis melo var. duripulposus; Cucumis melo var. hibernus; Cucumis melo var. makuwa; Cucumis melo var. microspermus; Cucumis microspermus; Cucumis momordica) and includes both wild accessions as well as cultivars. Cucumis melo is sometimes considered to consist of the subspecies Cucumis melo subsp. agrestis and Cucumis melo subsp. melo. The latter is then further sub-divided in the botanical varieties var. cantalupensis (also known as cantaloupe; muskmelon; netted melon; Persian melon; nutmeg melon), var. chito, var. flexuosus, var. inodorus, var. momordica (snap melon), var. reticulatis and var. texanus. Melon accession PI313970 as referred to herein, corresponds to Cucumis melo var. agrestis. This botanical variety is growing as weed in several African and Asian countries. This accession has the biological status "wild." Its fruits are inedible.

The term "cultivar" is used herein to denote a plant having a biological status other than a "wild" status, which "wild" status indicates the original non-cultivated, or natural state of a plant or accession. The term "cultivar" (for cultivated variety) includes, but is not limited to, semi-natural, semi-wild, weedy, traditional cultivar, landrace, breeding material, research material, breeder's line, synthetic population, hybrid, founder stock/base population, inbred line (parent of hybrid cultivar), segregating population, mutant/genetic stock, and advanced/improved cultivar. Examples of cultivars include such cultivated varieties that belong to the botanical groups Cucumis melo var. cantalupensis (the Charantais and Italian cantaloupe group), Cucumis melo var. reticulatis (the Galia and Ananas group), and Cucumis melo var. inodorus (including Piel de Sapo, Yellow Canary, Branco and Honeydew types). Therefore, a plant of the present in invention is preferably a plant of the melon botanical varieties cantalupensis, reticulatis or inodorus. The term "var." indicates a varietas (a taxonomic level below that of the species). A plant of the present invention is preferably not a Cucumis melo var. agrestis plant.

The term "a plant of melon accession PI313970" is used to indicate the source of the closterovirus-resistance QTL identified herein, and includes the accession as available from any of the public collections or depository institutions well know to the skilled artisan, as well as closterovirus-resistant derivatives thereof.

The term "closterovirus" as used herein refers to a virus of the family of Closteriviridae including, but not limited to, viruses commonly referred to as Cucurbit yellow stunting disorder virus (CYSDV), Lettuce infectious yellows virus (LIYV) and Beet pseudo-yellows virus (BPYV; also known under its synonyms Melon chlorotic spot virus (CCSV), Melon yellows virus, Muskmelon yellows virus or Strawberry pallidosis virus), preferably BPYV and CYSDV, most preferably CYSDV.

A "locus" is defined herein as the position that a given gene occupies on a chromosome of a given species.

As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes.

As used herein, the term "hybrid" means any offspring of a cross between two genetically unlike individuals, including but not limited to the cross between two inbred lines.

As used herein, the term "inbred" means a substantially homozygous individual or line.

As used herein, the terms "introgression," "introgressed" and "introgressing" refer to both a natural and artificial process whereby genes of one species, variety or cultivar are moved into the genome of another species, variety or cultivar, by crossing those species. The process may optionally be completed by backcrossing to the recurrent parent.

"Genetic engineering," "transformation" and "genetic modification" are all used herein as synonyms for the transfer of isolated and cloned genes into the DNA, usually the chromosomal DNA or genome, of another organism.

The terms "resistant" and "resistance" encompass both partial and full resistance to infection. A CYSDV-susceptible melon plant may either be non-resistant or have low levels of resistance to infection by CYSDV.

As used herein, the term "plant part" indicates a part of the melon plant, including single cells and cell tissues such as plant cells that are intact in plants, cell clumps and tissue cultures from which melon plants can be regenerated. Examples of plant parts include, but are not limited to, single cells and tissues from pollen, ovules, leaves, embryos, roots, root tips, anthers, flowers, fruits, stems shoots, and seeds; as well as pollen, ovules, leaves, embryos, roots, root tips, anthers, flowers, fruits, stems, shoots, scions, rootstocks, seeds, protoplasts, calli, and the like.

As used herein, the term "population" means a genetically heterogeneous collection of plants sharing a common genetic derivation.

As used herein, the term "cultivated variety" or "cultivar" means a group of similar plants that by structural or genetic features and/or performance can be distinguished from other cultivated varieties within the same species. The term "variety" without any specific indication may refer to both a botanical and a cultivated variety, and to either one depending on the context.

The term "QTL" is used herein in its art-recognised meaning. The term "QTL associated with resistance to CYSDV in melon" as well as the shorter term "QTL for CYSDV-resistance" refer to a region located on a particular chromosome of melon that is associated with at least one gene that encodes for CYSDV-resistance or at least a regulatory region, i.e. a region of a chromosome that controls the expression of one or more genes involved in CYSDV-resistance. The phenotypic expression of that gene may for instance be observed as a reduced rate of viral replication and/or as a reduced rate of viral movement through the plant. A QTL may for instance comprise one or more genes of which the products confer the genetic resistance. Alternatively, a QTL may for instance comprise regulatory genes or sequences of which the products influence the expression of genes on other loci in the genome of the plant thereby conferring the CYSDV-resistance. The QTL of the present invention (QTL-1) may be defined by indicating its genetic location in the genome of the respective wild *Cucumis* accession using one or more molecular genomic markers.

One or more markers, in turn, indicate a specific locus. Distances between loci are usually measured by frequency of crossing-over between loci on the same chromosome and expressed as centimorgan. The further apart two loci are, the more likely that a crossover will occur between them. Conversely, if two loci are close together, a crossover is less likely to occur between them. As a rule, one centimorgan (Kosambi map function (cM)) is approximately equal to 1% recombination between loci (markers) (Lui, 1997). When a QTL can be indicated by multiple markers the genetic distance between the end-point markers is indicative of the size of the QTL.

The term "CYSDV-susceptible recipient melon plant" is used herein to indicate a melon plant that is to receive DNA obtained from a donor melon plant that comprises a QTL for CYSDV-resistance. Said "CYSDV-susceptible recipient melon plant" may or may not already comprise one or more QTLs for CYSDV-resistance, in which case the term indicates a plant that is to receive an additional QTL.

The term "natural genetic background" is used herein to indicate the original genetic background of a QTL. Such a background is the genome of melon accession PI313970. Thus, melon accession PI313970 represent the natural genetic background of the QTL of the invention. Conversely, a method that involves the transfer of DNA comprising the QTL, or a resistance-conferring part thereof, from chromosome LG6 of melon accession PI313970 to the same position on the corresponding chromosome of another melon species, will result in that QTL, or said resistance-conferring part thereof, not being in its natural genetic background.

As used herein, the term "linkage group" refers to all of the genes or genetic traits that are located on the same chromosome. Within the linkage group, those loci that are close enough together will exhibit linkage in genetic crosses. Since the probability of crossover increases with the physical distance between genes on a chromosome, genes whose locations are far removed from each other within a linkage group may not exhibit any detectable linkage in direct genetic tests. The term "linkage group" is mostly used to refer to genetic loci that exhibit linked behaviour in genetic systems where chromosomal assignments have not yet been made. Thus, in the present context, the term "linkage group" is synonymous to (the physical entity of) chromosome.

As used herein, the term "molecular marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers, sequence-characterized amplified regions (SCARs), cleaved amplified polymorphic sequence (CAPS) markers or isozyme markers or combinations of the markers described herein which defines a specific genetic and chromosomal location. A "molecular marker linked to a QTL" as defined herein may thus refer to SNPs, insertion mutations as well as more usual AFLP markers or any other type of marker used in the field. In the context of AFLP markers named herein the markers indicate a melon-specific DNA sequence flanked by two AFLP-primers, which primers consist of "core primers" E and M, corresponding with the restriction sites of the restriction enzymes EcoRI and MseI, (Vos et al., 1995; Bai et al. 2003), each followed by a two-digit code identifying the selective nucleotides by which the "core primer" is extended (11: AA; 14: AT; 48: CAC; 49: CAG; 50: CAT; 51: CCA; 54: CCT; 57: CGG; 60: CTC). E11/M49-239 represents a marker obtained by using amplification primers EcoRI+AA and MseI+CAG to produce a fragment having a total length of 239 bp. which is the approximated size of the resulting polymorphic fragment (given size±1-2 basepairs). The size is normally rounded off but may also be given in decimals. The length of the fragment may depend on the method used to detect the fragment, and is an approximation of its true length.

The term "melon-specific DNA sequence" indicates a polynucleotide sequence having a nucleotide sequence homology of more than 80%, preferably more than 85%, more preferably more than 90%, even more preferably more than 95%, still more preferably more than 97%, most preferably more than 99% with a sequence of the genome of the species Cucumis melo that shows the greatest similarity to it, preferably in the case of markers for the QTL of the present invention, the part of the DNA sequence of melon accession PI313970 flanking the QTL-1 markers.

The term "nucleotide sequence homology" as used herein denotes the presence of homology between two polynucleotides. Polynucleotides have "homologous" sequences if the sequence of nucleotides in the two sequences is the same when aligned for maximum correspondence. Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence homology" for polynucleotides, such as 50, 60, 70, 80, 90, 95, 98, 99 or 100 percent sequence homology may be determined by comparing two optimally aligned sequences over a comparison window, wherein the portion of the polynucleotide sequence in the comparison window may include additions or deletions (i.e. gaps) as compared to the reference sequence (which does not comprise additions or deletions) for optimal alignment of the two sequences. The percentage is calculated by: (a) determining the number of positions at which the identical nucleic acid base occurs in both sequences to yield the number of matched positions; (b) dividing the number of matched positions by the total number of positions in the window of comparison; and (c) multiplying the result by 100 to yield the percentage of sequence homology. Optimal alignment of sequences for comparison may be conducted by computerized implementations of known algorithms, or by visual inspection. Readily available sequence comparison and multiple sequence alignment algorithms are, respectively, the Basic Local Alignment Search Tool (BLAST) (Altschul et al., 1990; Altschul et al., 1997) and ClustalW programs, both available on the internet. Other suitable programs include, but are not limited to, GAP, BestFit, PlotSimilarity, and FASTA in the Wisconsin Genetics Software Package (Genetics Computer Group (GCG), Madison, Wis., USA) (Devereux et al., 1984).

A quantitative trait locus (QTL) associated with resistance to closterovirus according to the present invention was first observed in a plant of melon accession PI313970. Upon AFLP analysis, and interval mapping of a large number of AFLP markers in the genome of crosses between PI313970 and commercial melon cultivars, the closterovirus-resistance-conferring QTL was found to be associated with markers E11/M54-156, E14/M54-152, E14/M51-210, E14/M51-083, E11/M49-239, E11/M54-169, E14/M50-262, E11/M57-278, E11/M54-163 and/or E11/M49-072, and was found to be located on the chromosome equivalent of linkage group (LG) 6 on a region spanning about 1.9 to about 17.2 cM.

The markers identified herein may be used is various aspects of the invention as will now be illustrated. Aspects of the invention are not be limited to the use of the markers identified herein. It is stressed that the aspects may also make use of markers not explicitly disclosed herein or even yet to be identified. Other than the genetic unit "gene," on which the phenotypic expression depends on a large number of factors that cannot be predicted, the genetic unit "QTL" denotes a region on the genome that is directly related to a phenotypic quantifiable trait. Thus, while genes per se bears little or no relation to plant breeding, a QTL is directly applicable to plant breeding. Now that no QTLs for closterovirus-resistance in melon were known prior to the filing of the present application, it follows that there was no industrial application of closterovirus-resistance genes in methods for plant breeding. The present inventors have now discovered a QTL for closterovirus-resistance in melon that is carried into offspring plants. The inventors made this discovery by observing that the presence of a string of contiguous genomic markers belonging to linkage group 6, i.e. on a single chromosome in the genome of melon correlated to the presence of a particular phenotypic trait that affected the occurrence of disease symptoms after exposure to an infectious amount of closterovirus viral particles in those melons and they showed that this genomic region was inherited according to normal Mendelian laws of inheritance.

The QTL first identified by the present inventors is located on chromosome identified herein as linkage group 6 and its location is best characterized by a number of otherwise arbitrary markers. In the present investigations amplified fragment length polymorphism (AFLP) markers were used, although restriction fragment length polymorphism (RFLP) markers, single nucleotide polymorphisms (SNPs), microsatellite markers (e.g. SSRs), sequence-characterized amplified region (SCAR) markers, cleaved amplified polymorphic sequence (CAPS) markers or isozyme markers or combinations of these markers might also have been used. In general, a QTL may span a region of several million bases. Therefore, providing the complete sequence information for the QTL is practically unfeasible but also unnecessary, as the way in which the QTL is first detected—through the observed correlation between the presence of a string of contiguous genomic markers and the presence of a particular phenotypic trait—allows one to trace amongst offspring plants those plants that have the genetic potential for exhibiting a particular phenotypic trait. By providing a non-limiting list of markers, the present invention thus provides for the effective utility of the QTL in a breeding program.

The QTL as described herein was found by crossing C. melo var. agrestis (PI 319370) with C. melo var. reticulatis (galia) and screening for resistance to CYSDV using a conventional bioassay (field-test under natural CYSDV pressure). LOD scores for AFLP markers significantly higher than 3 were considered to indicate the QTL.

A marker is specific for a particular line of breed. Thus, a specific trait is associated with a particular marker. The markers as indicated in the present application do not only indicate the location of the QTL, they also correlate to the presence of the specific phenotypic trait in a plant. It is important to note that the contiguous genomic markers that indicate the location of the QTL on the genome are in principal arbitrary or non-limiting. In general, the location of a QTL is indicated by a contiguous string of markers that exhibit statistical correlation to the phenotypic trait. Once a marker is found outside that string (i.e. one that has a LOD-score below a certain threshold, indicating that the marker is so remote that recombination in the region between that marker and the QTL occurs so frequently that the presence of the marker does not correlate in a statistically significant manner to the presence of the phenotype) the boundaries of the QTL are set. Thus, it is also possible to indicate the location of the QTL by other markers located within that specified region.

It is further important to note that the contiguous genomic markers can also be used to indicate the presence of the QTL (and thus of the phenotype) in an individual plant, i.e. they can be used in marker assisted selection (MAS) procedures. In principle, the number of potentially useful markers is limited but may be very large, and the skilled person may easily identify additional markers to those mentioned in the present application. Any marker that is linked to the QTL, e.g. falling within the physically boundaries of the genomic region spanned by the markers having established LOD scores above a certain threshold thereby indicating that no or very little recombination between the marker and the QTL occurs in crosses; as well as any marker in linkage disequilibrium to the QTL; as well as markers that represent the actual causal mutations within the QTL, may be used in MAS procedures. This means that the markers identified in the application as associated to the QTL, such as the AFLP marker E11/M49-239, are mere examples of markers suitable for use in MAS procedures. Moreover, when the QTL, or the specific trait-conferring part thereof, is introgressed into another genetic background (i.e. into the genome of another plant species), then some markers may no longer be found in the offspring although the trait is present therein, indicating that such markers are outside the genomic region that represents the specific trait-conferring part of the QTL in the original parent line only and that the new genetic background has a different genomic organisation.

Thus, a method for producing a plant of the present invention comprising introgressing into a closterovirus-susceptible melon plant the closterovirus-resistance-conferring QTL from melon accession PI313970, and involving MAS procedures, is not limited to the use of markers that are provided herein for the sole purpose of (roughly) indicated the location of the QTL in the chromosome. The skilled person knows that other markers may provide at least equal utility in such MAS procedures.

The causal mutation of the QTL, i.e. a mutation in the DNA comprised in the QTL, which e.g. results in a change in a protein-coding sequence or affects the expression of a gene in a manner that leads to the observed phenotype, is not always identified. This in itself is, however, of no consequence to the invention as any of the markers associated with the QTL and present in a screened plant indicates the presence of the causal mutation in that plant.

Because reliable and reproducible disease assays that would enable the identification and localization of genetic material responsible for conferring closterovirus-resistance are time consuming, the use of markers linked to the QTL identified herein will aid in breeding for closterovirus-resistance in melon.

The nucleic acid sequence of a QTL of the present invention may be determined by methods known to the skilled person. For instance, a nucleic acid sequence comprising said QTL or a resistance-conferring part thereof may be isolated from a closterovirus-resistant donor plant by fragmenting the genome of said plant and selecting those fragments harboring one or more markers indicative of said QTL. Subsequently, or alternatively, the marker sequences (or parts thereof) indicative of said QTL may be used as (PCR) amplification primers, in order to amplify a nucleic acid sequence comprising said QTL from a genomic nucleic acid sample or a genome fragment obtained from said plant. The amplified sequence may then be purified in order to obtain the isolated QTL. The nucleotide sequence of the QTL, and/or of any additional markers comprised therein, may then be obtained by standard sequencing methods.

The present invention therefore also relates to an isolated nucleic acid (preferably DNA) sequence that comprises a QTL of the present invention, or a closterovirus-resistance-conferring part thereof. Thus, the markers that pinpoint the various QTLs described herein may be used for the identification, isolation and purification of one or more genes from melon that encode for closterovirus resistance.

The nucleotide sequence of a QTL of the present invention may for instance also be resolved by determining the nucleotide sequence of one or more markers associated with said QTL and designing internal primers for said marker sequences that may then be used to further determine the sequence the QTL outside of said marker sequences. For instance the nucleotide sequence of the AFLP markers identified herein may be obtained by isolating said markers from the electrophoresis gel used in the determination of the presence of said markers in the genome of a subject plant, and determining the nucleotide sequence of said markers by for instance dideoxy chain terminating methods, well known in the art.

In embodiments of such methods for detecting the presence of a QTL in a suspected closterovirus-resistant melon plant, the method may also comprise the steps of providing a oligonucleotide or polynucleotide capable of hybridizing under stringent hybridization conditions to a nucleic acid sequence of a marker linked to said QTL, preferably selected from the markers identified herein as being linked to said QTL, contacting said oligonucleotide or polynucleotide with a genomic nucleic acid of a suspected closterovirus-resistant melon plant, and determining the presence of specific hybridization of said oligonucleotide or polynucleotide to said genomic nucleic acid. Preferably said method is performed on a nucleic acid sample obtained from said suspected closterovirus-resistant melon plant, although in situ hybridization methods may also be employed. Alternatively, and in a more preferred embodiment, the skilled person may, once the nucleotide sequence of the QTL has been determined, design specific hybridization probes or oligonucleotides capable of hybridizing under stringent hybridization conditions to the nucleic acid sequence of said QTL and may use such hybridization probes in methods for detecting the presence of a QTL of the invention in a suspected closterovirus-resistant melon plant.

The phrase "stringent hybridization conditions" refers to conditions under which a probe or polynucleotide will hybridize to its target subsequence, typically in a complex mixture of nucleic acids, but to essentially no other sequences. Stringent conditions are sequence-dependent and will be different in different circumstances. Longer sequences hybridize specifically at higher temperatures. An extensive guide to the hybridization of nucleic acids is found in Tijssen (Tijssen, 1993). Generally, stringent conditions are selected to be about 5-10° C. lower than the thermal melting point (Tm) for the specific sequence at a defined ionic strength pH. The $T_m$ is the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. Additional guidelines for determining hybridization parameters are provided in numerous references, e.g. *Current Protocols in Molecular Biology*, Eds. Ausubel, et al. 1995).

"Nucleic acid" or "oligonucleotide" or "polynucleotide" or grammatical equivalents used herein means at least two nucleotides covalently linked together. Oligonucleotides are typically from about 7, 8, 9, 10, 12, 15, 18 20 25, 30, 40, 50 or up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphosphoroamidite linkages (see Eckstein, 1991), and peptide nucleic acid backbones and linkages. Mixtures of naturally occurring nucleic acids and analogs can be used. Particularly preferred analogs for oligonucleotides are peptide nucleic acids (PNA).

Production of Closterovirus-Resistant Melon Plants by Transgenic Methods

A closterovirus-resistant melon plant, or part thereof, according to the present invention comprises within its genome a QTL associated with closterovirus-resistance, or a closterovirus-resistance-conferring part thereof, as defined herein above and derived from melon accession PI313970 wherein said QTL or said closterovirus-resistance-conferring part thereof is not in its natural genetic background. Such a plant may be obtained by using various methods well known in the art, either transgenic or non-transgenic.

According to another aspect of the present invention, a nucleic acid (preferably DNA) sequence comprising the QTL of the present invention or a closterovirus-resistance-conferring part thereof, may be used for the production of a closterovirus-resistant melon plant. In this aspect, the invention provides for the use of a QTL of to the present invention or closterovirus-resistance-conferring parts thereof, for producing a closterovirus-resistant melon plant, which use involves the introduction of a nucleic acid sequence comprising said QTL in a closterovirus-susceptible recipient melon plant. As stated, said nucleic acid sequence may be derived from a suitable closterovirus-resistant donor melon plant. A suitable closterovirus-resistant donor melon plant capable of providing a nucleic acid sequence comprising the hereinbefore-described QTL, or closterovirus-resistance-conferring part thereof, is *Cucumis melo* accession PI313970. Other related melon plants that exhibit resistance to closterovirus and comprise one or more genes that encode for closterovirus resistance may also be utilized as closterovirus-resistance donor plants as the present invention describes how this material may be identified. Other accessions of *Cucumis melo* can be examined for closterovirus-resistance either by using bioassay screens or by using MAS procedures with a marker specific for the QTL described herein.

A QTL of the present invention was first discovered in *Cucumis melo* accession PI313970, however, also other melon accession may be screened for the presence of this QTL. Once identified in a suitable donor melon plant, the nucleic acid sequence that comprises a QTL for closterovirus-resistance according to the present invention, or a closterovirus-resistance-conferring part thereof, may be transferred to a suitable recipient plant by any method available. For instance, the said nucleic acid sequence may be transferred by crossing a closterovirus-resistance donor melon plant with a susceptible recipient melon plant, or even a plant of another genus, (i.e. by introgression), by transformation, by protoplast fusion, by a doubled haploid technique or by embryo rescue or by any other nucleic acid transfer system, optionally followed by selection of offspring plants comprising the QTL and exhibiting closterovirus-resistance. For transgenic methods of transfer a nucleic acid sequence comprising a QTL for closterovirus-resistance according to the present invention, or a closterovirus-resistance-conferring part thereof, may be isolated from said donor plant by using methods known in the art and the thus isolated nucleic acid sequence may be transferred to the recipient plant by transgenic methods, for instance by means of a vector, in a gamete, or in any other suitable transfer element, such as a ballistic particle coated with said nucleic acid sequence.

Plant transformation generally involves the construction of an expression vector that will function in plant cells. In the present invention, such a vector comprises a nucleic acid sequence that comprises a QTL for closterovirus-resistance of the present invention, or a closterovirus-resistance-conferring part thereof, which vector may comprise a closterovirus-resistance-conferring gene that is under control of or operatively linked to a regulatory element, such as a promoter. The expression vector may contain one or more such operably linked gene/regulatory element combinations, provided that at least one of the genes contained in the combinations encodes for closterovirus-resistance. The vector(s) may be in the form of a plasmid, and can be used, alone or in combination with other plasmids, in a method for producing transgenic plants that are resistant to closterovirus, using transformation methods known in the art, such as the *Agrobacterium* transformation system.

Expression vectors can include at least one marker (reporter) gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the marker gene). Many commonly used selectable marker genes for plant transformation are known in the art, and include, for example, genes that code for enzymes that metabolically detoxify a selective chemical agent which may be an antibiotic or a herbicide, or genes that encode an altered target which is insensitive to the inhibitor. Several positive selection methods are known in the art, such as mannose selection. Alternatively, marker-less transformation can be used to obtain plants without mentioned marker genes, the techniques for which are known in the art.

One method for introducing an expression vector into a plant is based on the natural transformation system of *Agrobacterium* (see e.g. Horsch et al., 1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant (see e.g. Kado, 1991). Methods of introducing expression vectors into plant tissue include the direct infection or co-cultivation of plant cells with *Agrobacterium tumefaciens* (Horsch et al., 1985). Descriptions of *Agrobacterium* vectors systems and methods for *Agrobacterium*-mediated gene transfer provided by Gruber and Crosby, 1993 and Moloney et al., 1989. See also, U.S. Pat. No. 5,591,616. General descriptions of plant expression vectors and reporter genes and transformation protocols and descriptions of *Agrobacterium* vector systems and methods for *Agrobacterium*-mediated gene transfer can be found in Gruber and Crosby, 1993. General methods of culturing plant tissues are provided for example by Miki et al., 1993 and by Phillips, et al., 1988. A proper reference handbook for molecular cloning techniques and suitable expression vectors is Sambrook and Russell (2001).

Another method for introducing an expression vector into a plant is based on microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes (See, Sanford et al., 1987, 1993; Sanford, 1988, 1990; Klein et al., 1988, 1992). Another method for introducing DNA to plants is via the sonication of target cells (see Zhang et al., 1991). Alternatively, liposome or spheroplast fusion has been used to introduce expression vectors into plants (see e.g. Deshayes et al., 1985 and Christou et al., 1987). Direct uptake of DNA into protoplasts using $CaCl_2$ precipitation, polyvinyl alcohol or poly-L-ornithine has also been reported (see e.g., Hain et al. 1985 and Draper et al., 1982). Electroporation of protoplasts and whole cells and tissues has also been described (D'Halluin et al., 1992 and Laursen et al., 1994).

Following transformation of melon target tissues, expression of the above described selectable marker genes allows for preferential selection of transformed cells, tissues and/or plants, using regeneration and selection methods now well known in the art. The AFLP markers as identified herein may also be used for that purpose.

Production of Closterovirus-Resistant Melon Plants by Non-Transgenic Methods

In an alternative embodiment for producing a closterovirus-resistant melon plant, protoplast fusion can be used for the transfer of nucleic acids from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell, that may even be obtained with plant species that cannot be interbreeded in nature, is tissue cultured into a hybrid plant exhibiting the desirable combination of traits. More specifically, a first protoplast can be obtained from a melon plant or other plant line that exhibits resistance to infection by closterovirus. A second protoplast can be obtained from a second melon or other plant line, preferably a melon line that comprises commercially valuable characteristics, such as, but not limited to disease resistance, insect resistance, valuable fruit characteristics, etc. The protoplasts are then fused using traditional protoplast fusion procedures, which are known in the art.

Alternatively, embryo rescue may be employed in the transfer of a nucleic acid comprising one or more QTLs as described herein from a donor plant to a recipient plant. Embryo rescue can be used as a procedure to isolate embryo's from crosses wherein plants fail to produce viable seed. In this process, the fertilized ovary or immature seed of a plant is tissue cultured to create new plants (Pierik, 1999).

The present invention also relates to a method of producing a closterovirus-resistant melon plant comprising the steps of performing a method for detecting the presence of a quantitative resistance locus (QTL) associated with resistance to closterovirus in a donor melon plant according to invention as described above, and transferring a nucleic acid sequence comprising at least one QTL thus detected, or a closterovirus-resistance-conferring part thereof, from said donor plant to a closterovirus-susceptible recipient melon plant. The transfer of said nucleic acid sequence may be performed by any of the methods previously described herein.

A preferred embodiment of such a method comprises the transfer by introgression of said nucleic acid sequence from a closterovirus-resistant donor melon plant into a closterovirus-susceptible recipient melon plant by crossing said plants. This transfer may thus suitably be accomplished by using traditional breeding techniques. QTLs are preferably introgressed into commercial melon lines by using marker-assisted breeding (MAS). Marker-assisted breeding or marker-assisted selection involves the use of one or more of the molecular markers for the identification and selection of those offspring plants that contain one or more of the genes that encode for the desired trait. In the present instance, such identification and selection is based on selection of QTLs of the present invention or markers associated therewith. MAS can also be used to develop near-isogenic lines (NIL) harboring the QTL of interest, allowing a more detailed study of each QTL effect and is also an effective method for development of backcross inbred line (BIL) populations (see e.g. Nesbitt et al., 2001; van Berloo et al., 2001). Melon plants developed according to this embodiment can advantageously derive a majority of their traits from the recipient plant, and derive closterovirus-resistance from the donor plant.

As discussed briefly above, traditional breeding techniques can be used to introgress a nucleic acid sequence encoding for closterovirus-resistance into a closterovirus-susceptible recipient melon plant. In one method, which is referred to as pedigree breeding, a donor melon plant that exhibits resistance to closterovirus and comprising a nucleic acid sequence encoding for closterovirus-resistance is crossed with a closterovirus-susceptible recipient melon plant that preferably exhibits commercially desirable characteristics, such as, but not limited to, disease resistance, insect resistance, valuable fruit characteristics, etc. The resulting plant population (representing the $F_1$ hybrids) is then self-pollinated and set seeds ($F_2$ seeds). The $F_2$ plants grown from the $F_2$ seeds are then screened for resistance to closterovirus. The population can be screened in a number of different ways.

First, the population can be screened using a traditional disease screen. Such disease screens are known in the art. Preferably a quantitative bioassay is used. Second, marker-assisted selection can be performed using one or more of the hereinbefore-described molecular markers to identify those progeny that comprise a nucleic acid sequence encoding for closterovirus-resistance. Other methods, referred to hereinabove by methods for detecting the presence of a QTL may be used. Also, marker-assisted selection can be used to confirm the results obtained from the quantitative bioassays, and therefore, several methods may also be used in combination.

Inbred closterovirus-resistant melon plant lines can be developed using the techniques of recurrent selection and backcrossing, selfing and/or dihaploids or any other technique used to make parental lines. In a method of recurrent selection and backcrossing, closterovirus-resistance can be introgressed into a target recipient plant (the recurrent parent) by crossing the recurrent parent with a first donor plant, which differs from the recurrent parent and is referred to herein as the "non-recurrent parent." The recurrent parent is a plant that is non-resistant or has a low level of resistance to closterovirus and possesses commercially desirable characteristics, such as, but not limited to (additional) disease resistance, insect resistance, valuable fruit characteristics, etc. The non-recurrent parent exhibits closterovirus resistance and comprises a nucleic acid sequence that encodes for closterovirus-resistance. The non-recurrent parent can be any plant variety or inbred line that is cross-fertile with the recurrent parent. The progeny resulting from a cross between the recurrent parent and non-recurrent parent are backcrossed to the recurrent parent. The resulting plant population is then screened for the desired characteristics, which screening may occur in a number of different ways. For instance, the population can be screened using phenotypic pathology screens or quantitative bioassays as known in the art. Alternatively, in stead of using bioassays, marker-assisted selection (MAS) can be performed using one or more of the hereinbefore described molecular markers, hybridization probes or polynucleotides to identify those progeny that comprise a nucleic acid sequence encoding for closterovirus-resistance. Also, MAS can be used to confirm the results obtained from the quantitative bioassays. In case the QTL is located on a recessive locus, this means that the resistance gene cannot be screened in an $F_1$ or $BC_1$ population by using phenotypic screens such as resistance bioassays. The markers defined herein are therefore ultimately suitable to select proper offspring plants by genotypic screening.

Following screening, the $F_1$ hybrid plants that exhibit a closterovirus-resistant phenotype or, more preferably, genotype and thus comprise the requisite nucleic acid sequence encoding for closterovirus-resistance are then selected and backcrossed to the recurrent parent for a number of generations in order to allow for the melon plant to become increasingly inbred. This process can be performed for two to five or more generations. In principle the progeny resulting from the process of crossing the recurrent parent with the closterovirus-resistance non-recurrent parent are heterozygous for one or more genes that encode for closterovirus-resistance.

It should be brought into mind that, for instance when introgressing a recessive locus the resistant phenotype will only occur in offspring plants under conditions wherein homozygous plants can be formed.

In general, a method of introducing a desired trait into a hybrid melon variety comprises the steps of:

(a) crossing an inbred melon parent with another melon plant that comprises one or more desired traits, to produce F1 progeny plants, wherein the desired trait is selected from the group consisting of closterovirus resistance-resistance;

(b) selecting said F1 progeny plants that have the desired trait to produce selected F1 progeny plants, preferably using molecular markers as defined herein;

(c) backcrossing the selected progeny plants with said inbred melon parent plant to produce backcross progeny plants;

(d) selecting for backcross progeny plants that have the desired trait and morphological and physiological characteristics of said inbred melon parent plant, wherein said selection comprises the isolation of genomic DNA and testing said DNA for the presence of at least one molecular marker for QTL-1, preferably as described herein;

(e) repeating steps (c) and (d) two or more times in succession to produce selected third or higher backcross progeny plants;

(f) optionally selfing selected backcross progeny in order to identify homozygous plants (g) crossing at least one of said backcross progeny or selfed plants with another inbred melon parent plant to generate a hybrid melon variety with the desired trait and all of the morphological and physiological characteristics of hybrid melon variety when grown in the same environmental conditions.

As indicated, the last backcross generation may be selfed in order to provide for homozygous pure breeding (inbred) progeny for closterovirus-resistance. Thus, the result of recurrent selection, backcrossing and selfing is the production of lines that are genetically homogenous for the genes associated with closterovirus-resistance as well as other genes associated with traits of commercial interest.

Closterovirus-Resistant Melon Plants and Seeds

The goal of plant breeding is to combine in a single variety or hybrid various desirable traits. For commercial crops, these traits may include resistance to diseases and insects, tolerance to heat and drought, reducing the time to crop maturity, greater yield, and better agronomic quality. Uniformity of plant characteristics such as germination and stand establishment, growth rate, maturity, and plant height may also be of importance.

Commercial crops are bred through techniques that take advantage of the plant's method of pollination. A plant is self-pollinated if pollen from one flower is transferred to the same or another flower of the same plant. A plant is sib pollinated when individuals within the same family or line are used for pollination. A plant is cross-pollinated if the pollen comes from a flower on a different plant from a different family or line.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of heterogeneous plants that differ genetically and will not be uniform.

The development of a hybrid melon variety in a melon plant breeding program involves three steps: (1) the selection of plants from various germplasm pools for initial breeding crosses; (2) the selfing of the selected plants from the breeding crosses for several generations to produce a series of inbred lines, which, individually breed true and are highly uniform; and (3) crossing a selected inbred line with an unrelated inbred line to produce the hybrid progeny (F1). After a sufficient amount of inbreeding successive filial generations will merely serve to increase seed of the developed inbred. Preferably, an inbred line should comprise homozygous alleles at about 95% or more of its loci.

An important consequence of the homozygosity and homogeneity of the inbred lines is that the hybrid created by crossing a defined pair of inbreds will always be the same. Once the inbreds that create a superior hybrid have been identified, a continual supply of the hybrid seed can be produced using these inbred parents and the hybrid melon plants can then be generated from this hybrid seed supply.

A closterovirus-resistant melon plant, or a part thereof, obtainable by a method of the invention is an aspect of the present invention.

Another aspect of the present invention relates to a closterovirus-resistant melon plant, or part thereof, comprising the QTLs in any configuration as described in detail above wherein at least one of said QTLs is not in its natural genetic background. The closterovirus-resistant melon plants of the present invention can be of any genetic type such as inbred, hybrid, haploid, dihaploid or transgenic. Further, the plants of the present invention may be heterozygous or homozygous for the resistance traits, preferably homozygous. Although the QTLs of the present invention, as well as resistance-conferring parts thereof may be transferred to any plant in order to provide for a closterovirus-resistant plant, the methods and plants of the invention are preferably related to plants of the species Cucumis melo.

The closterovirus-resistant inbred melon lines described herein can be used in additional crossings to create closterovirus-resistant hybrid plants. For example, a first closterovirus-resistant inbred melon plant of the invention can be crossed with a second inbred melon plant possessing commercially desirable traits such as, but not limited to, disease resistance, insect resistance, desirable fruit characteristics, etc. This second inbred melon line may or may not be closterovirus-resistant.

Another aspect of the present invention relates to a method of producing seeds that can be grown into closterovirus-resistant melon plants. In one embodiment, the method comprises the steps of providing a closterovirus-resistant melon plant of the invention, crossing said closterovirus-resistant plant with another melon plant, and collecting seeds resulting from said cross, which when planted, produce closterovirus-resistant melon plants.

In another embodiment, the method comprises the steps of providing a closterovirus-resistant melon plant of the invention, crossing said closterovirus-resistant plant with a melon plant, collecting seeds resulting from said cross, regenerating said seeds into plants, selecting closterovirus-resistant plants by any of the methods described herein, self-pollinating the selected plants for a sufficient number of generations to obtain plants that are fixed for an allele that confers closterovirus-resistance in the plants, backcrossing the plants thus produced with melon plants having desirable phenotypic traits for a sufficient number of generations to obtain melon plants that are closterovirus-resistant and have desirable phenotypic traits, and collecting the seeds produced from the plants resulting from the last backcross, which when planted, produce melon plants which are closterovirus-resistant.

REFERENCES

Altschul S F, Gish W, Miller W, Myers E W, Lipman D J (1990) "Basic local alignment search tool," *J. Molec. Biol.*, 215:403-410.

Altschul S F, Madden T L, Schaffer A A, Zhang J, Zhang Z, Miller W, Lipman D J (1997) "Gapped BLAST and PSI-BLAST: A new generation of protein database search programs," *Nucl. Acids Res.*, 25:3389-3402.

Bai Y L, Huang C C, van der Hulst R, Meijer Dekens F, Bonnema G, Lindhout P (2003) "QTLs for melon powdery mildew resistance (*Oidium lycopersici*) in *Lycopersicon parviflorum* G1.1601 co-localize with two qualitative powdery mildew resistance genes," *Mol. Plant. Microbe Interactions*, 16:169-176.

Christou P, Murphy J E, and Swain W F (1987) "Stable transformation of soybean by electroporation and root formation from transformed callus," *Proc. Natl. Acad. Sci. USA*, 84:3962-3966.

Deshayes A, Herrera-Estrella L, Caboche M (1985) Liposome-mediated transformation of tobacco mesophyll protoplasts by an *Escherichia coli* plasmid. *EMBO J.*, 4:2731-2737.

D'Halluin K, Bonne E, Bossut M, De Beuckeleer M, Leemans J (1992) *Plant Cell*, 4:1495-1505.

Draper J, Davey M R, Freeman J P, Cocking E C and Cox B J (1982) "Ti plasmid homologous sequences present in tissues from *Agrobacterium* plasmid-transformed Petunia protoplasts," *Plant and Cell Physiol.*, 23:451-458.

Eckstein F (Ed.) (1991) *Oligonucleotides and Analogues, A Practical Approach.*, Oxford Univ. Press, NY 1991.

Gruber M Y, Crosby W L (1993) "Vectors for plant transformation," *Methods in Plant Molecular Biology and Biotechnology*, B R Glick, J E Thompson, Eds., CRC Press, Baton Rouge, La., pp. 89-119.

Hain R, Stabel P, Czernilofsky A P, Steinbliss H H, Herrera-Estrella L, Schell J (1985) "Uptake, integration, expression and genetic transmission of a selectable chimeric gene to plant protoplasts," *Mol. Gen. Genet.*, 199:161-168.

Horsch R B, Fraley R T, Rogers S G, Sanders P R, Lloyd A (1985) "A simple and general method for transferring genes into plants," *Science*, 227:1229-1231.

Kado C I (1991) "Molecular mechanisms of crown gall tumorigenesis," *Crit. Rev. Plant Sci.*, 10:1-32.

Klein T M, Arentzen R, Lewis P A, and Fitzpatrick-McElligott S (1992) "Transformation of microbes, plants and animals by particle bombardment," *Bio/Technology*, 10:286-291.

Laursen C M, Krzyzek R A, Flick C E, Anderson P C, Spencer T M (1994) "Production of fertile transgenic maize by electroporation of suspension culture cells," *Plant Mol. Biol.*, 24(1):51-61.

López-Sesé A I, Gómez-Guillamón M L (2000) "*Cucurbit yellow stunting disorder virus* (CYSDV) in *Cucumis melo* L," *Hortscience*, 35:110-113.

Lui B H (1997) *Statistical Genomics: Linkage, Mapping, and QTL Analysis*, CRC Press, Boca Raton, Fla.

Miki B L, Fobert P F, Charest P J, Iyer V N (1993) "Procedures for Introducing Foreign DNA into Plants," *Methods in Plant Molecular Biology & Biotechnology*, Glick B R and Thompson J E (Eds.) CRC Press, pp. 67-88.

Moloney M M, Walker J M, Sharma K K (1989) "High efficiency transformation of *Brassica napus* using *Agrobacterium* vectors," *Plant Cell Rep.*, 8:238-242.

Nesbitt T C, Tanksley S D (2001) "fw2.2 directly affects the size of developing tomato fruit, with secondary effects on fruit number and photosynthate distribution,"*Plant Physiol.*, 127:575-583.

Phillips R L, Somers D A, Hibberd K A (1988) "Cell/tissue culture and in vitro manipulation," *Corn and Corn Improvement*, 3rd ed., pp. 345-387, G. F. Sprague & J. W. Dudley (Eds.), Madison, Wis., USA, American Society of Agronomy.

Sambrook J, and Russell D W (2001) *Molecular Cloning: A Laboratory Manual*, New York, N.Y., USA, Cold Spring Harbor Laboratory Press.

Sanford J C, Klein T M, Wolf E D, Allen N (1987) "Delivery of substances into cells and tissues using a particle bombardment process," *J. Particulate Sci. Technol.*, 5:27-37.

Sanford J C (1988) "The biolistic process," *Trends in Biotechnology*, 6:299-302.

Sanford J C (1990) "Biolistic plant transformation," *Physiologica Plantarum*, 79:206-209.

Sanford J C, Smith F D, and Russell J A (1993) "Optimizing the biolistic process for different biological applications," *Methods in Enzymology*, 217:483-509.

Tijssen P (1993) "Hybridization With Nucleic Acid Probes. Part I. Theory and Nucleic Acid Preparation," *Laboratory Techniques in Biochemistry and Molecular Biology*, Elsevier.

Van Berloo R, Aalbers H, Werkman A, Niks R E (2001) "Resistance QTL confirmed through development of QTL-NILs for barley leaf rust resistance," *Mol. Breeding*, 8:187-195.

Vos P, Hogers R, Bleeker M, Reijans M, van de Lee T, Hornes M, Frijters A, Pot J, Peleman J, Kuiper M (1995) "AFLP: a new technique for DNA fingerprinting," *Nucl. Acids Res.*, 23:4407-4414.

Zhang L, Cheng L, Xu N, Zhao M, Li C, Yuan J, and Jia S (1991) "Efficient transformation of tobacco by ultrasonication," *Biotechnology*, 9:996-997.

The invention claimed is:

1. A Cucurbit Yellow Stunting Disorder Virus (CYSDV)-resistant plant of the species *Cucumis melo*, said plant comprising a homozygous genetic element from a plant of melon accession PI 313970, which genetic element comprises a CYSDV-resistance-conferring QTL located on a chromosome equivalent to linkage group (LG) 6 of melon accession PI 313970, that stretches from position 25.5 cM to 29.1 cM between AFLP markers E11/M54-156 and E11/M57-278, wherein said QTL is indicated by the presence of at least two AFLP markers linked to said QTL selected from the group consisting of markers E11/M54-156, E14/M54-152, E14/M51-210, E11/M49-239, and E11/M54-169, and the absence of at least one AFLP marker selected from the group consisting of markers E14/M50-262, E14/M51-083, and E11/M49-072, wherein said plant is not melon accession PI 313970.

2. The plant according to claim 1, wherein said plant of the species *Cucumis melo* is a melon cultivar or a plant of the group consisting of botanical varieties *Cucumis melo* var. *cantalupensis*, *Cucumis melo* var. *reticulatis* and *Cucumis melo* var. *inodorus*.

3. The plant according to claim 1, wherein said genetic element is an introgression.

4. The plant according to claim 1, wherein said plant is a CYSDV-resistant melon cultivar.

5. The plant according to claim 1, wherein said plant is an inbred plant or hybrid plant.

6. A part of a plant as defined in claim 1.

7. The plant part according to claim 6, wherein said plant is an inbred plant or hybrid plant and said plant part is a seed or fruit.

8. A method of producing a CYSDV-resistant melon plant comprising the step of transferring a nucleic acid comprising the CYSDV-resistance-conferring QTL on melon linkage group 6 (LG6) located between markers E11/M54-156 and E11/M57-278, or a CYSDV-resistance-conferring part thereof comprising at least one CYSDV-resistance conferring gene, from a CYSDV-resistant donor melon plant of melon accession PI 313970, or a CYSDV-resistant derivative thereof to a CYSDV-susceptible recipient melon plant, wherein said transfer of said nucleic acid is performed by transformation, by protoplast fusion, by a doubled haploid technique or by embryo rescue.

9. A method of producing a CYSDV-resistant melon plant, said method comprising the steps of:
a) introgressing a nucleic acid comprising the CYSDV-resistance-conferring QTL on melon linkage group 6 (LG6) located between markers E11/M54-156 and E11/M57-278, or a CYSDV-resistance-conferring part thereof comprising at least one CYSDV-resistance conferring gene, from a CYSDV-resistant plant of melon accession PI 313970, or a CYSDV-resistant derivative thereof, to a CYSDV-susceptible recipient melon plant; and
b) determining the presence of said CYSDV-resistance-conferring QTL in the genome of at least one progeny plant by detecting the presence in the DNA of said at least one progeny plants of at least one AFLP marker indicating said QTL wherein said marker is selected from the group formed by E11/M54-156, E14/M54-152, E14/M51-210, E11/M49-239, E11/M54-169, E11/M57-278, and E11/M54-163, and by detecting the absence in the DNA of said at least one progeny plants of at least one AFLP marker selected from the group consisting of E14/M51-083, E14/M50-262, and E11/M49-072.

10. The method according to claim 9, wherein said step a) comprises the steps of:
crossing a CYSDV-resistant plant of melon accession PI 313970, or a CYSDV-resistant derivative thereof, with a CYSDV-susceptible melon plant;
harvesting seed from said cross;
growing said seed to produce F1 progeny plants;
selfing or backcrossing said F1 progeny plants with the donor or recipient parent to produce F2 seeds, and growing said F2 seeds to produce F2 progeny plants.

11. The method according to claim 10, wherein the detection of said molecular marker linked to said QTL is performed in an F2 progeny plant.

12. The method according to claim 9, wherein said CYSDV-susceptible recipient melon plant is a plant selected from the group consisting of botanical varieties *Cucumis melo* var. *cantalupensis*, *Cucumis melo* var. *reticulatis* and *Cucumis melo* var. *inodorus*.

13. The method according to claim 8, further comprising selecting from among the offspring plants a plant that comprises in its genome said at least one QTL, or CYSDV-resistance-conferring part thereof.

14. The method according to claim 13, wherein said selection comprises the marker-assisted selection with a marker linked to said QTL.

15. A CYSDV-resistant melon plant, or part thereof, obtainable by a method according to claim 8, wherein the plant or part thereof comprises the CYSDV-resistance-conferring QTL, wherein said QTL is indicated by the presence of at least two AFLP markers linked to said QTL selected from the group consisting of markers E11/M54-156, E14/M54-152, E14/M51-210, E11/M49-239, and E11/M54-169, and the absence of at least one AFLP marker selected from the group consisting of markers E14/M50-262, E14/M51-083, and E11/M49-072, wherein said plant is not melon accession PI 313970.

16. A hybrid melon plant, or part thereof, obtainable by crossing a melon plant according to claim 1 with a melon plant that exhibits commercially desirable characteristics.

17. A melon seed produced by growing the melon plant according to claim 1.

18. A method of detecting a CYSDV-resistant melon plant comprising detecting presence of at least one marker selected from the group consisting of markers E11/M54-156, E14/M54-152, E14/M51-210, E11/M49-239, E11/M54-169, E11/M57-278, and E11/M54-163, and detecting absence of at least one marker selected from the group consisting of E14/M50-262, E14/M51-083, and E11/M49-072 in the DNA of the plant.

19. The plant of claim 1, wherein the plant is of the species *Cucumis melo* subspecies *melo*.

20. The CYSDV-resistant melon plant, or part thereof of claim 15, wherein the CYSDV-resistant melon plant is of the species *Cucumis melo* subspecies *melo*.

* * * * *